United States Patent [19]

Jessel, Jr. et al.

[11] Plant 4,981

[45] Feb. 8, 1983

[54] CARNATION PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 272,375

[22] Filed: Jun. 10, 1981

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—Schwartz, Jeffery, Schwaab, Mack, Blumenthal & Koch

[57] ABSTRACT

A carnation plant known by the cultivar name Jack and particularly characterized as to uniqueness by the combined characteristics of commercial double flower type; flat flower form, twisting slightly with maturity; medium flower size; red flower color with minimum color oxidation; medium flowering response; 5 to 7 flowers and buds showing color per flowering stem; medium peduncle length; strong peduncle strength; and medium plant height.

2 Drawing Figures

The present invention comprises a new and distinct cultivar of *Dianthus caryophyllus*, L., hereinafter referred to by the name Jack.

Jack is the product of a planned breeding program which had the objective of creating new spray type carnation cultivars in a wide color range with fast flowering response, unrestricted breaking action, vigorous growth, strong non-brittle stems, high bud and flower count, and attractive, durable flowers for year-round commercial production.

Jack was originated from a cross made in Barberton, Ohio in the year 1974. The male parent was Red Baron (#61740E53; unpatented; commercially available). The female parent was an unnamed red seedling, a product of the breeding program of the present inventors.

Jack was discovered and selected as one flowering plant within a progeny of the stated parentage by Walter H. Jessel, Jr. and William E. Duffett on July 18, 1975 in a controlled environment in Barberton, Ohio.

The first act of asexual reproduction of Jack was accomplished when vegetative cuttings were taken from the initial selection in October, 1975 in a controlled environment in Barberton, Ohio by a technician working under formulations established and supervised by Walter H. Jessel, Jr. and William E. Duffett. Horticultural examination of selected units initiated June 13, 1977 has demonstrated that the combination of characteristics as herein disclosed for Jack are firmly fixed and are retained through successive generations of asexual reproduction.

Jack has not been observed under all possible environmental conditions. The phenotype may vary significantly with variations in environment such as temperature, light intensity, and daylength. The following observations, measurements and comparisons describe plants grown in Salinas, Calif. under greenhouse conditions which approximate those generally used in commercial practice.

The following traits have been repeatedly observed and are determined to be basic characteristics of Jack which in combination distinguish this carnation as a new and distinct cultivar:

1. Commercial double flower type.
2. Flat flower form, twisting slightly with maturity.

3. Medium flower size, ranging from 55 to 65 mm. in diameter.
4. Red flower color with minimum color oxidation.
5. Medium flowering response.
6. 4 to 7 flowers and buds showing color per flowering stem.
7. Medium peduncle length, ranging from 8 to 10 cm.
8. Strong peduncle strength.
9. Medium plant height.

Of the several commercially available carnations known to the present inventors, the most similar in comparison to Jack is Red Baron. Reference is made to Chart A which compares selected characteristics of Jack with those same characteristics of Red Baron. General comparisons are as follows:

1. In comparison to Red Baron, Jack has brighter, more vivid color, larger average flower size, 1–2 less buds and flowers per stem, earlier flowering response, and shorter plant height. The general flower color tonality, and peduncle strength of Jack are similar to those same characteristics of Red Baron.

The accompanying photographic drawings illustrate typical foliage and inflorescence characteristics of Jack. Sheet 1 is a color photograph of Jack. Sheet 2 is a black and white photograph showing three views of the inflorescence of Jack. Colors are as nearly true as possible with illustrations of this type.

In the following description, color references are made to A Limit Color Cascade, by the Munsell Company, 1972 edition. The color values were determined between 4:30 and 5:00 P.M. on June 13, 1977 under 150 foot-candle light intensity at Salinas, Calif.

Classification:

*Botanical.*—*Dianthus caryophyllus*, L. Jack.

*Commercial.*—Spray carnation for cut flower production.

Inflorescence characteristics:

*Flowering response.*—Medium, ranging from 22 weeks (at Salinas, Calif. grown pinched from a July 5 plant date) to 30 weeks (at Barberton, Ohio grown pinched from an October 22 plant date).

*Inflorescence type.*—Semi-compound spray, with 1–4 buds per lateral, with reduced bud count during lower light periods; occasionally seen as a terminal spray, with 1 bud per lateral, especially on second cropping.

*Number of buds and flowers per stem.*—4 to 7 showing color on first crop.

*Peduncle length.*—Medium, ranging from 8 to 10 cm. on top flower.

*Peduncle strength.*—Strong, holding flowers erect in all periods; shows tendency toward brittleness during low light periods.

*Flower.*—Size: Medium, ranging from 55 to 65 mm. in diameter when grown as a spray; too small for adoption as a commercial disbud. Type: Commercial double, petals from 25 to 30 in number. Form: Flat, twisting slightly with maturity.

*Corolla.*—Smooth texture, both abaxial and adaxial; deeply serrated petal margin.

*Corolla color.*—General tonality from a distance of 3 meters: Red, approximately 40-12. Abaxial: Approximately 37-12 to 37-11. Adaxial: Approximately 37-11 to 37-10 streaked over 37-4. Keeping quality: On plant, up to 18 days; as a cut flower up to 15 days under room temperature of 20° C. Fragrance: Very slight to none, typical carnation. Reproductive organs: Androecium: Typical carnation, normal in all respects; long filament length, moderate to abundant pollen. Gynoecium: Typical carnation, normal in all respects; white pistil of medium length, approximately 30 to 32 mm.

Plant characteristics:

*Growth and duration.*—Bushy and vigorous semi-erect perennial; typical of cultivars adaptable to commercial cut spray production.

*Branching pattern.*—Semi-erect and unrestricted at base of plant.

*Height.*—Medium, 60 to 70 cm. at time of first cut grown as a pinched plant.

*Stem.*—Strong, with bend of 5 to 10 degrees (Society of American Florist's Standards), almost brittle during low light periods; approximately 50 to 55 cm. in length from top to first vegetative lateral.

*Foliage.*—Occurrence: Abundant; typical carnation. Color (Abaxial): Approximately 21-14 to 21-15 but more greyed. Color (Adaxial): Approximately 21-13 to 21-14 but more greyed.

CHART A

COMPARISON OF JACK AND RED BARON

| CULTIVAR | FLOWER COLOR | FLOWER SIZE | NO. OF BUDS AND FLOWERS PER STEM | FLOWERING RESPONSE PERIOD |
|---|---|---|---|---|
| Jack | Red | Medium 55 to 65 mm. | 4 to 7 | Medium from 22 to 30 weeks |
| Red Baron | Scarlet Red to Brick Red | Medium 45 to 65 mm. | 6 to 8 | Slow, from 25 to 34 weeks |

| CULTIVAR | PEDUNCLE LENGTH | PEDUNCLE STRENGTH | PLANT HEIGHT |
|---|---|---|---|
| Jack | Medium 8 to 10 cm. | Strong | Medium 60 to 70 cm. |
| Red Baron | Medium 10 to 12 cm. | Strong almost Brittle | Tall, 80 to 85 cm. |

COMPARISON MADE OF PINCHED, FLOWERING PLANTS GROWN IN SALINAS, CALIFORNIA

We claim:

1. A new and distinct cultivar of *Dianthus caryophyllus,* L. known by the cultivar name Jack, as described and illustrated, and particularly characterized as to uniqueness by the combined characteristics of commercial double flower type; flat flower form, twisting slightly with maturity; medium flower size, red flower color with minimum color oxidation; medium flowering response; 4 to 7 flowers and buds showing color per flowering stem; medium peduncle length; strong peduncle strength; and medium plant height.

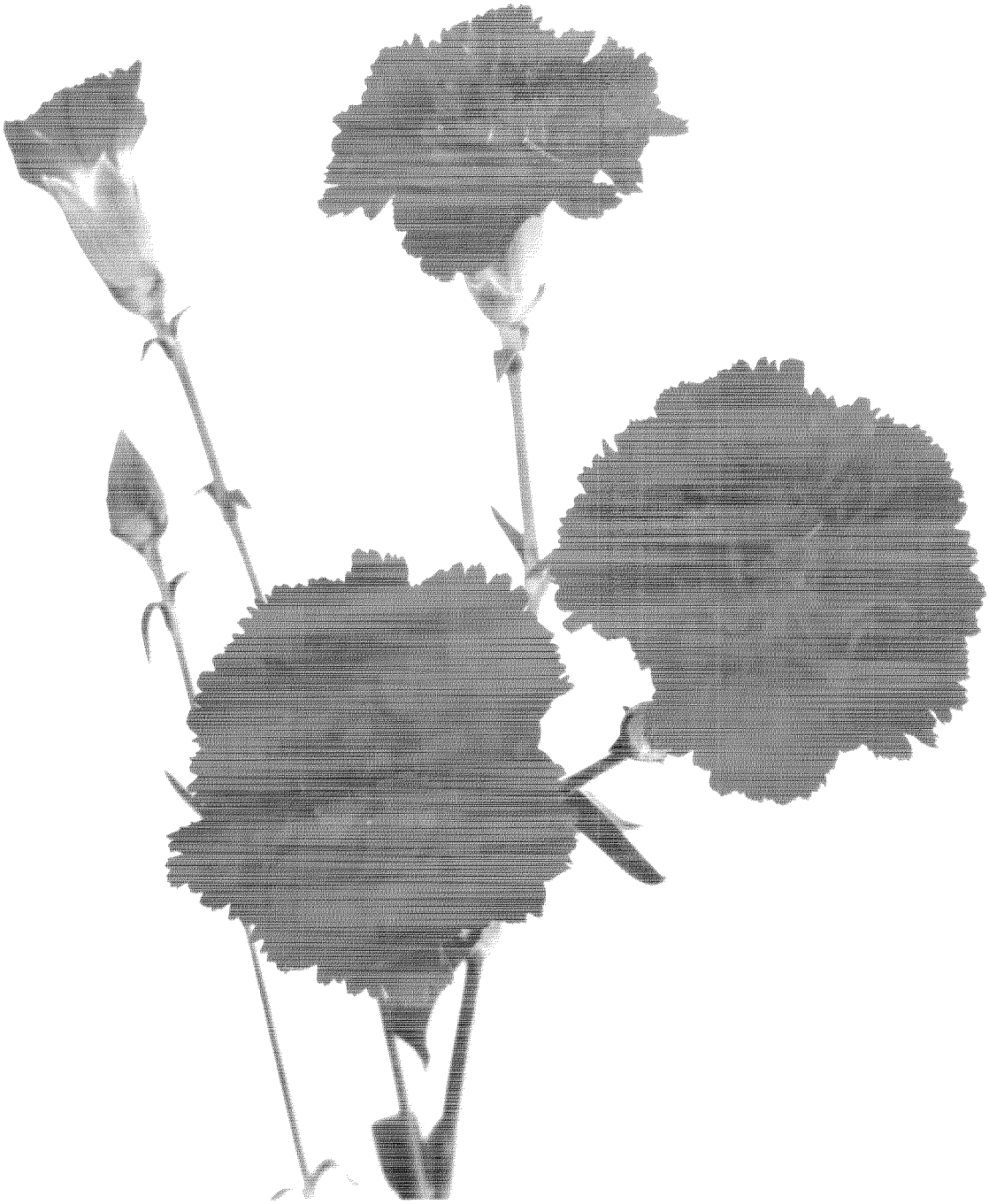

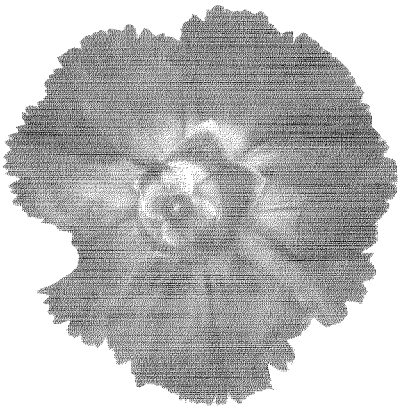
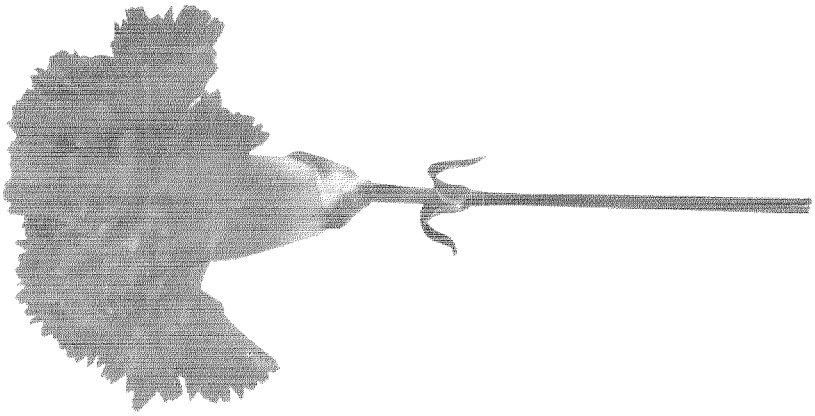
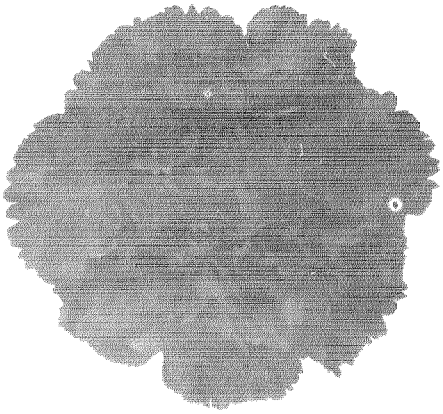

* * * * *